United States Patent [19]

Sabin et al.

[11] Patent Number: 4,952,396

[45] Date of Patent: Aug. 28, 1990

[54] METHOD OF USING PHYTIC ACID FOR INHIBITING TUMOR GROWTH

[75] Inventors: Robert Sabin, Goosedown Estate, Horseshoe Rd., Mill Neck, Long Island, N.Y. 11765; Raxit Jariwalla, Mountain View; Stephen Lawson, Menlo Park, both of Calif.

[73] Assignees: Linus Pauling Institute of Science & Medicine, Palo Alto, Calif.; Robert Sabin, Long Island, N.Y.

[21] Appl. No.: 205,140

[22] Filed: Jun. 10, 1988

Related U.S. Application Data

[63] Continuation-in-part of Ser. No. 932,661, Nov. 19, 1986, abandoned.

[51] Int. Cl.$^5$ .................... A61K 37/54; A61K 31/66
[52] U.S. Cl. .................................. 424/946; 514/102; 514/103
[58] Field of Search ................... 424/94.6; 435/196; 514/102, 103

[56] References Cited

U.S. PATENT DOCUMENTS

| | | | |
|---|---|---|---|
| 2,834,678 | 5/1958 | Hanson | 424/94.6 |
| 4,154,824 | 5/1979 | Bodor et al. | 514/103 |

OTHER PUBLICATIONS

Van Rensburg et al., Cited in Chem. Abstracts, vol. 94:45903d (1981).

*Primary Examiner*—Jacqueline M. Stone
*Attorney, Agent, or Firm*—Flehr, Hohbach, Test, Albritton & Herbert

[57] ABSTRACT

A method is provided for inhibiting tumor growth by administering to a subject an effective tumor-inhibiting amount of a compound selected from the group consisting of phytic acid, phytate salt, an isomer or hydrolysate of phytic acid or phytate salt, or a mixture of any combination thereof. The preferred method of administration is by oral dosages of about 2 to 4 grams/kilogram bodyweight per day.

10 Claims, 1 Drawing Sheet

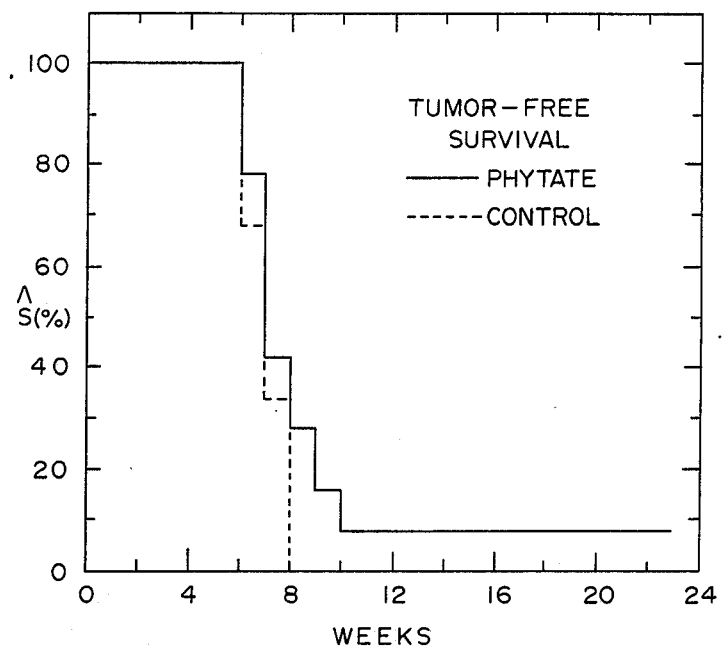
FIG.—1
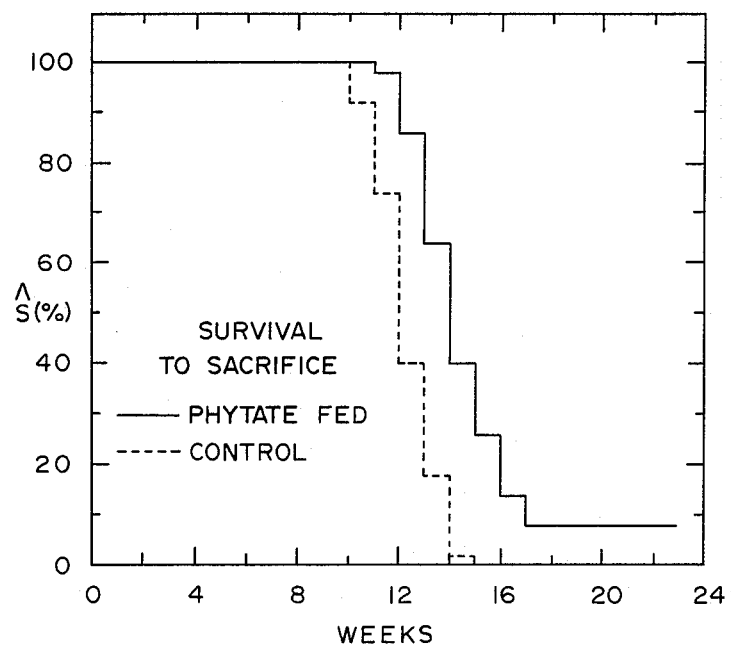
FIG.—2

METHOD OF USING PHYTIC ACID FOR INHIBITING TUMOR GROWTH

This is a continuation-in-part of our copending application Ser. No. 932,661, filed Nov. 19, 1986, now abandoned.

The present invention is directed to a method for inhibiting tumor growth by use of phytic acid, its salts or hydrolysates.

BACKGROUND OF THE INVENTION

Phytic acid, generally accepted as having the structure myo-inositol-hexakis (dihydrogen phosphate), is a major component of plant seeds, constituting 1–3% by weight of many cereals and oil seeds. Most wheat brans contain between 4 and 5% phytic acid. Phytic acid may be prepared in pure form from various plant sources, such as wheat, corn, soybeans, sesame seeds, peanuts, lima beans, barley, oats, wild rice and sunflower seeds. It can be extracted with dilute hydrochloric acid at room temperature, precipitated with various reagents including ferric chloride, bicarbonates, potassium hydroxide, sodium hydroxide, ammonium hydroxide, calcium hydroxide, magnesium hydroxide or alcohol. It is then further purified by conventional chemical techniques.

When one or more of the acidic protons of the phosphate groups in phytic acid are replaced by a counterion, the compound is usually referred to as a phytate salt. The special name phytin is used for the calcium-magnesium salt of phytate derived from plant seeds (a product of Ciba-Geigy). The present invention includes the use not only of phytic acid and phytate salts, but also various isomeric forms of phytic acid and phytate salts. While the Anderson structure for myo-inositol hexakis dihydrogen phosphate is the accepted structure for phytic acid, the present invention covers other isomers which have been previously described in the literature. These isomers include the cis, epi, allo, muco, neo, D-chiro, L-chiro, and scyllo configurations.

Also, while phytic acid contains six phosphate groups, when introduced into the digestive tract of an animal, one or more of the phosphate groups may be hydrolyzed by the action of the digestive acids and enzymes. Therefore, the present invention includes the use of hydrolysates of phytic acid and phytate salts wherein one or more of the phosphate groups have been removed.

The main uses of phytic acid include use as a food additive for preservation of foods. Studies on the use of phytic acid as a food additive show that ingestion of large doses of phytic acid elicits no physiological discomfort or symptoms of any toxicological action in humans. See Starkenstein, *Biochem. Z.* 30: 56 (1911). Phytic acid and its metabolites are thus not believed to be toxic or highly reactive.

Medical applications of phytic acid include use as an imaging agent for organ scintography, an X-ray enhancement contrasting agent and use to reduce gastric secretion for treatment of gastritis, gastroduodenitis, gastric duodenal ulcers and diarrhea. It has been suggested as an antidote for toxic metal absorption, for therapeutic use in the prevention and dilution of calcium deposits associated with various diseases and for reducing calcium concentration in urine (thus checking the formation of renal calculi). Other uses include as a preventive agent against severe poisoning with pressurized oxygen and preventing thirst during exercise. It has been used as a counterion in salts with various orally administered antibiotics to improve taste.

Phytic acid has also been suggested to reduce the incidence of dental caries, and has been utilized in dentifrices, mouth rinses, dental cements, cleaning agents for dentures and for removing nicotine tar from teeth.

Industrial uses of phytic acid include use as a corrosion inhibitor on metals, a rust remover and an additive to lubricating greases. Other miscellaneous uses of phytic acid include oral administration to treat acne, to improve skin color, blood circulation and fingernail growth; and as an additive in cosmetics for anti-dandruff hair lotions and skin care lotions. One potential agricultural use of phytic acid is to inhibit aflatoxin production by *Asperoillus parasiticus*. It is also useful as an additive to a fermentation medium containing *Micromonospora sagamiensis* in the fermentative production of antibiotics. Similarly, phytic acid may be used as a growth-promoting factor in the fermentation medium for the cultivation of yeast for feed.

For further discussions of industrial applications of phytic acid, see Graf, *JAOCS* 60, 1861–1867 (1983).

Although the above description indicates the broad scope of potential uses of phytic acid, there is not believed to be any suggestion in the prior art that phytic acid is useful for the inhibition of tumor growth.

Accordingly, it is an object of the present invention to provide a method for inhibiting tumor growth by use of phytic acid, phytate salts, and isomers or hydrolysates thereof.

This and other objects will be made apparent by the following description of the preferred embodiments and appended claims.

DESCRIPTION OF THE FIGURES

FIG. 1 is a graph measuring the percent of rats surviving (Kaplan-Meier, tumor-free survival S) as a function of time (in weeks) for rats injected with tumorigenic, CMV-transformed cell line (N=50 for each group). Phytate treatment group exhibited decreased hazard to tumor appearance compared to control group (see data below).

FIG. 2 is a graph of the percentage of rats surviving (Kaplan-Meier, survival to sacrifice) as a function of time (in weeks) for rats injected with tumorigenic, CMV-transformed cell line (N=50 for each group. Phytate treatment group exhibited significantly improved survival compared to control group (p-value=0.0000).

SUMMARY OF THE INVENTION

The present invention provides a method of inhibiting tumor growth, comprising the step of administering to a subject a tumor-inhibiting dose of a compound, selected from the group consisting of phytic acid, a phytate salt, an isomer or hydrolysate of phytic acid or a phytate salt, or a mixture of any combination thereof. The preferred method of administration is by the oral route.

DESCRIPTION OF THE PREFERRED EMBODIMENTS

The method according to the present invention comprises treating a subject, known or suspected to be afflicted with tumors, with a composition in which the active ingredient is phytic acid, a phytate salt, or an isomer or hydrolysate of phytic acid or phytate salt. By the term isomer as used herein, it is intended to include the various conformations of phytic acid, as described hereinabove, and the corresponding conformations of phytate salts. The term salts is broadly intended to cover any of the various salts formed by the replacement of any or all of the available acidic protons of the phosphate groups with a counterion. The counterion may be any pharmaceutically acceptable counterion such as sodium, magnesium, potassium, zinc, ferric, ferrous, and the like, including organic counterions such as quaternary ammonium ions and ions of organic bases. The present invention also includes the hydrolysates of phytic acid and phytate salts wherein one or more of the phosphate groups have been removed. Once administered into the digestive tract, bloodstream or tumor site in the subject, the phytic acid or phytate salt may be hydrolyzed by digestive, blood or cellular enzymes, thereby removing one or more of the phosphate groups on the cyclohexane ring. However, it is contemplated to be within the scope of the invention that these hydrolysates of phytic acid and phytate salts may also be administered directly to the subject and therefore are within the scope of the present invention.

The hydrolysates of phytic acid and phytate salts may be prepared by partial acid or basic hydrolysis or by hydrolysis using enzymes prior to preparation of dosage forms for administration. Preferably, the hydrolysates will be made in vivo by coadministering with phytic acid or phytate salt an enzyme which hydrolyzes phosphate groups, such as 3-phytase, 6-phytase and acid phosphatase, which are commonly identified by this enzyme nomenclature as recommended by IUPAC-IUB.

The phytic acid or phytate salt may be absorbed into or adsorbed onto a solid carrier to facilitate pharmaceutical administration. For example, phytic acid may be formulated into a starch powder by spray drying or vacuum drying an aqueous mixture of phytic acid and dextrin.

The preferred composition for administration in oral dosage form is the monopotassium phytate salt, which may be prepared from commercially and readily available sodium phytate by initially removing the sodium using ion exchange chromatography on a suitable resin, such as Dowex beads. The free phytic acid may then be treated with potassium hydroxide to convert to the monopotassium phytate salt.

The preferred method of administration of the compositions according to the present invention is through oral administration in liquid or tablet form. As described hereinabove, the compositions may be administered as pharmaceutically acceptable salts such as salts with alkali metal cations (sodium, potassium, lithium), ammonium salts and salts with organic bases such as piperidine, triethanolamine, diethylaminoethylamine salts, and the like.

It is preferred that the phytate salt be administered in accordance with the present invention in conjunction with a low calcium diet. Therefore an animal (rat) subject will also be orally coadministered about 0.02 to 0.08 wt. % calcium in the diet during treatment with the phytate. In human subjects, the calcium diet is preferably limited to 100–600 mg. Ca/day. The efficacy of inhibition of tumor growth is believed to reach its optimum by combining the phytate treatment and low calcium diet.

In addition to the active ingredients, the composition may also contain an effective proportion, usually from 0.001 to 0.1% weight by volume, of a pharmaceutically acceptable preservative or sterilizing agent such as cetyl pyridinium chloride, tetradecyltrimethyl ammonium bromide (commercially known as Centramide), benzyl dimethyl [2-(2-)p-(1,1,3,3-tetramethyl butyl)) phenoxy) ethoxy] ammonium chloride (known commercially as Benzethonium Chloride) and myristyl-gamma-picolinium chloride.

The pharmaceutical composition may also contain conventional excipients, e.g., sodium chloride, dextrose, mannitol, and buffers such as sodium dihydrogen ortho phosphate, disodium hydrogen phosphate, sodium citrate/citric acid, and boric acid/sodium borate. The proportion and concentration of excipients and buffers may be varied within fairly wide ranges, providing the resulting solution is stable and nonirritating when administered. The preferred method of administration is by oral administration as a solid compound. The composition may be prepared in the conventional manner as tablets, pills or powders, using conventional carriers.

Any method of administration may be utilized which will ultimately bring the phytic acid, phytate salts, isomer or hydrolysate thereof into contact with the tumor or tumor cells. The method of administration of choice may therefore depend upon the site of the tumor and/or extent of tumor growth.

The dosage to be administered will vary with the location and severity of the tumor growth. However, in general, particularly for oral administration, oral administration of from 2 to 4 grams of phytic acid (or equivalent phytate salt, isomer or hydrolysate) per kilogram of body weight in the diet per day will usually be effective. Frequency of dosage administration may, of course, be varied as needed and as discretionarily required by the attending physician.

The present invention provides compositions which inhibit tumor growth, and in some cases, even prevent tumor growth, both effects of which lead to prolonged survival of the subject afflicted with the tumor.

For oral administration, in a preferred embodiment, the active ingredient of the composition will also contain an enzyme such as 3-phytase (EC 3.1.38), 6-phytase (EC 3.1.3.26) or acid phosphatase which, when exposed to the digestive tract, will assist in hydrolyzing one or more of the phosphate groups from the active ingredient. While not intending to be limited by any theory, it is believed that at the tumor site, removal of phosphate groups is preferred, and it may even be required, to effect the tumor-inhibiting activity. Since phytic acid or phytate salts are not naturally present in animals, the digestive enzymes in animals are believed to be insufficient to completely hydrolyze the phosphate groups. The amount of enzyme administered will be dependent upon the subject's ability to digest the phytate, thus, dosages may be routinely adjusted by the physician in accordance with the subject's needs. Therefore, to enhance the hydrolysis of the phosphate groups in an animal or man, it is preferred that the active ingredient be administered with one or more of the aforementioned enzymes, with the preferred enzyme being 3-phytase (EC 3.1.3.8).

Alternatively, as a substitute for or in conjunction with administration of a hydrolyzing enzyme, the subject may be treated with an activated antibody which, functionally, serves as an enzyme.

The invention is illustrated but in no way limited by the following example.

EXAMPLE

Fisher strain rats (100 animals) were randomized into two diet groups of 50 animals. The control diet consisted of normal lab chow supplemented with magnesium oxide (MgO). The experimental diet consisted of normal lab chow supplemented with MgO and 12% by weight tetrapotassium dimagnesium phytate (referred to in this example as "phytate"). The MgO was solely added to conform to the Mg molar ratio occurring in natural phytate in aleurone particles of rice. Furthermore, magnesium has been demonstrated to be the activating ion for the hydrolyzing enzyme phytase present in intestines. Each of the groups (comprising 50 rats) was further randomized into 10 cages with 5 rats per cage. The NIH guidelines were followed for housing and care of all animals. Animals were acclimated to normal lab chow, then put on stepwise increases of transition diet for a week, then switched to the respective full-strength diet (12% phytate or control). After 2 weeks, all animals were randomly injected subcutaneously with $1 \times 10^6$ cells per animal using a tumorigenic rat cell line. The tumorigenic line was derived following in vitro transformation of Rat-2 cells by DNA-transfection with a cloned fragment (XbaI/BamHI-EM) from human cytomegoloviris strain Towne (El-Beik, T., et al., *J. Virology* Vol. 60:645–652 1986). Cultures initiated and expanded from frozen stocks were used for cell injection. After inoculation, respective diets were continued for a total period of 23 weeks. All data were monitored and entered into coded forms by technicians who were blinded as to which groups the rats belonged. Body weights were recorded once every two weeks and tumor diameters (length and width) were measured once a week. The latent period for tumor appearance and the time to reach a terminal tumor size of 4 centimeters were determined. If a rat survived until tumor size reached 4 centimeters, the rat was sacrificed.

DATA ANALYSIS

Four endpoints are computed and analyzed:
1. Tumor incidence.
2. Time to tumor appearance (i.e., tumor-free survival).
3. Time to reach 4 cm limit tumor size (i.e., survival to sacrifice).
4. Rate of tumor growth.

ANALYSIS FOR TUMOR INCIDENCE

At any week the data can be displayed in a $2 \times 3$ "contingency table."

| Group | 0 | Tumor Size >0 cm, <4 cm | ≧4 cm | Total |
|---|---|---|---|---|
| N | $n_{11}$ | $n_{12}$ | $n_{13}$ | 50 |
| X | $n_{21}$ | $n_{22}$ | $n_{23}$ | 50 |

$n_{ij}$ = number of rats in tumor-size group j and diet group i (N or X). The X group is the phytate fed group, N is the control group. There is a natural ordering of the columns in this table. An appropriate analysis uses a two-sample t-test for ordered categories. Scores are assigned to categories which reflect the natural ordering. For a given study duration, the value of the two sample t-statistic is computed under the hypothesis of no difference between the groups. This value of t, with 98 degrees of freedom, can be referred to the normal distribution.

| Results for Tumor Incidence | | |
|---|---|---|
| | Significance | |
| Duration (weeks) | t-statistic | Level |
| 7 | −.82 | .4 |
| 10 | −2.92 | .004 |
| 13 | −7.81 | .0000 |
| 16 | −2.67 | .008 |
| 19 | −2.06 | .04 |
| 23 | −2.06 | .04 |

| Examples of data | | | |
|---|---|---|---|
| Group | 0 | Tumor Size | >4 cm |
| 7 weeks: | | | |
| | | >0, <4 cm | |
| N | 17 | 33 | 0 |
| X | 21 | 29 | 0 |
| 13 weeks: | | | |
| N | 0 | 9 | 41 |
| X | 4 | 28 | 18 |
| 23 weeks: | | | |
| | | >4 cm | |
| N | 0 | 0 | 50 |
| X | 4 | 0 | 46 |

Incidence is computed as the average of the scores for each group.

Conclusion: From the tenth week on, tumor incidence in X group is significantly lower than in control group.

Analysis for Survival

The analysis for tumor-free survival (i.e., time until tumor appearance) and survival to sacrifice (i.e., time until the largest diameter reaches 4 cm) is identical in form.

For illustrative purposes, the Kaplan-Meier survival curves for groups N and X are displayed (FIGS. 1 and 2). The Mantel-Haenzel (or log-rank) test is used to make a statistical comparison.

There are reasons to believe that inferences about "survival" times may not be valid unless one accounts for changes in each individual rat's body weight. Previous experiments have shown that diet restriction is associated with increased survival. Therefore a Cox proportional hazards model was used to test for significance in hazard rates between the groups "controlling for" changes in body weight.

Formally, the proportional hazard model is given by $$h/t;20) = ho/t) \exp\{\beta_1 X_2 + \beta_2 X_w\}$$

where
$X = (X_2, X_w)$,
$X_2 = \{1$ if rat belongs to the X group, 0 otherwise$\}$
$X_w$ is the estimate of the slope of the regression line fitted through a rat's weight data recorded until a tumor is palpated (t = latent period for a tumor appearance), or until a diameter reached 4 cm (t = time to reach 4 cm tumor diameter). ho/t is the (unknown) hazard function for the chow plus MgO group; i.e., group N.

If the estimate of $\beta_1$ is statistically significant, then there is evidence that there is a difference in hazard in group X compared to group N whether or not the estimate of $b_w$ is significant. Thus, statements about statistical significance remain valid as we have controlled for changes in body weight.

Results for Tumor-Free Survival (time to tumor appearance)

1. Mantel-Haenzel test: value of test statistic=1.924. This is not significant at the 0.05 level (p-value 0.054) [not adjusted for weight].
2. Cox:

| Variable | estimate of Coefficient | SDT Error | p-value |
|---|---|---|---|
| group X ($X_2$) | −.475 | .224 | .034 |
| rate of change of body weight ($X_w$) | +.116 | .112 | .301 |

Thus, when we control for weight, group X is of decreased hazard to tumor appearance compared to group N (p-value=0.034).

Results for Survival to Sacrifice (time to sacrifice)

1. Mantel-Haenzel test: value of test statistic=4.92. This is significant at the 0.0000 level of significance.
2. Cox

| Variable | Estimate of Coefficient | STD Error | p-value |
|---|---|---|---|
| group X ($X_2$) | −1.143 | .234 | .0000 |
| $X_w$ | +.019 | .147 | .90 |

Thus, when we control for Weight, group X is at decreased hazard to tumor reaching diameter of 4 cm compared to group N (p-value=0.0000).

It is interesting to note that the X group is statistically significantly at lower hazard to tumor appearance than the control group only if one controls for weight (p=0.034 versus p=0.054). Since the estimate of the coefficient for rate of change in body weight is positive, the Cox results suggest (although not significantly as p=0.301) that the hazard of tumor appearance is higher for those rats with increased rate of change of body weight.

A two-sample t-test was performed in order to compare X group and control mean body weight growth rates (up to tumor appearance). The results are summarized below:

| Group | Sample Size | Mean Body Weight Growth Rate gms/wk | Standard Error |
|---|---|---|---|
| Control | 50 | 2.37 | .142 |
| Group X | 50 | 2.92 | .150 |

The value of the t-statistic is −2.66 and is significant at the 0.1 level. The group X had a mean body weight growth rate which was significantly higher than that of the control group. Adjusting for these differences resulted in group X being at a statistically significantly lower (p=0.034) hazard to tumor appearances.

For time to sacrifice, the estimate of the coefficient for the rate of change in body weight is close to zero. In this case, the coefficient is highly non-significant (p=0.9). Nevertheless, a two-sample t-test comparing mean growth rates (up to a tumor diameter reaching 4 cm) gave the following results:

| Group | Sample Size | Mean Body Weight Growth Rate gms/wk | Standard Error |
|---|---|---|---|
| control | 50 | 2.90 | .119 |
| Group X | 50 | 3.26 | .096 |

The value of the t-statistic is −2.35 is significant at the 0.2 level. Thus, even though the mean growth rates appear to be different for the two groups, there was no effect of body weight growth rates on the hazard function.

Analysis for Tumor Growth Rate

Once a tumor has appeared, the area of the tumor can be calculated, at weekly intervals, until the rat is either sacrificed (tumor diameter at least 4 cm) or the study terminated. By least squares, a straight line was fitted through each rat's "area of tumor" data. The slope of this line, $b_i$, is the estimated tumor growth rate for the rat i in diet group j.

$$b_1 = \sum_{i=1}^{50} b_{i1}/50 \text{ and } b_2 = \sum_{i=1}^{50} b_{i2}/50$$

are the average tumor growth rates for the control and X groups, respectively.

The average tumor growth rates are then compared by using the two-sample t-tests.

Results for Tumor Growth Rate

| Group | Sample Size | Mean Tumor Area Growth Rate cm/wk | Standard Error |
|---|---|---|---|
| Control | 50 | .665 | .021 |
| Group X | 50 | .457 | .026 |

The value of the t-statistic is 6.18 and is significant at the 0.0001 level. Thus, the average growth rate of group X is highly significantly lower than the control group value.

Referring to FIG. 1, there are shown two tumor-free survival curves, the solid line representing the experimental group fed a diet supplemented with 12% phytate, and the dotted line representing the control group. As can be seen from FIG. 1, for the first 6 weeks there are no deaths in the control group and experimental group. From the 6th to the 8th week both groups exhibited deaths (by sacrifice or as a result of tumors); however, the experimental group which was fed phytate had fewer deaths. By the 8th week, the entire control group died (i.e., all had either succumbed to the tumor or experienced tumor growth to over 4 centimeters) whereas a significant portion (over 25%) of the experimental group survived. From the 8th to the 10th week, more of the experimental group were sacrificed due to the tumor growth, but subsequent to the 10th week a certain proportion of the experimental group (about 8%) continued with tumor-free survival. This test shows that the phytate treatment group exhibited a significantly decreased hazard of tumor appearance compared to the control group (P value=0.034) after controlling for changes in body weight as discussed above. In particular from the 6th through the 10th week the experimental group showed that tumor growth was inhibited versus the control group and subsequent to the 10th week the experimental group showed tumor-free survival whereas all of the control group at that point had died or been sacrificed.

Referring to FIG. 2, there is a plot of the percent of survival-to-sacrifice of the two groups as a function of time in weeks from injection of the tumorigenic cells. Statistical analysis shows that the phytate-treated group exhibited significantly improved survival compared to the control group (P-value=0.0000). Again, subsequent to the 17th week, a finite number of the experimental group survived without appearance of tumors.

We claim:

1. A method of inhibiting tumor fibrosarcoma growth comprising the step of administering to a subject an effective tumor-inhibiting amount of a compound selected from the group consisting of phytic acid, a phytate salt, an isomer or hydrolysate of phytic acid or a phytate salt, or a mixture of any combination thereof.

2. A method according to claim 1 wherein said phytate salt comprises its monopotassium salt.

3. A method according to claim 1 further comprising the step of coadministering to said subject a low calcium diet consisting of 100 to 600 mg calcium per day during treatment of said subject.

4. A method according to claim 1 wherein said phytic acid is absorbed into a pharmaceutically acceptable carrier.

5. A method according to claim 1 wherein said isomers of phytic acid or phytate salt comprise the hexakisphosphate myo-inositol, scyllo-inositol, D-chiro-inositol, L-chiro-inositol, neo-inositol and muco-inositol conformations.

6. A method according to claim 5 wherein said isomer of phytic acid or phytate salt is the hexakisphosphate myo-inositol conformation.

7. A method according to claim 1 wherein said hydrolysate of phytic acid or phytate salt comprises the pentakisphosphate, tetrakisphosphate, triphosphate, diphosphate, monophosphate or completely dephosphorylated hydrolysate.

8. A method according to claim 1 wherein said compound is administered orally in combination with a dephosphorylating enzyme.

9. A method according to claim 8 wherein said enzyme is 3-phytase, 6-phytase, acid phosphatase, or any combination thereof.

10. A method according to claim 9 wherein said enzyme is 3-phytase EC 3.1.3.8.

* * * * *